United States Patent
Truitt

(10) Patent No.: US 8,497,403 B2
(45) Date of Patent: Jul. 30, 2013

(54) CONDENSATION OF DIOLS FOR BIOFUEL PRODUCTION

(75) Inventor: Matthew J. Truitt, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 13/312,729

(22) Filed: Dec. 6, 2011

(65) Prior Publication Data
US 2012/0157732 A1   Jun. 21, 2012

Related U.S. Application Data

(60) Provisional application No. 61/424,775, filed on Dec. 20, 2010, provisional application No. 61/438,299, filed on Feb. 1, 2011.

(51) Int. Cl.
*C10G 1/00* (2006.01)

(52) U.S. Cl.
USPC ............. 585/240; 585/242; 44/605; 44/606

(58) Field of Classification Search
None
See application file for complete search history.

(56) References Cited

U.S. PATENT DOCUMENTS

| | | |
|---|---|---|
| 6,228,789 B1 | 5/2001 | Wu et al. |
| 7,049,476 B1 | 5/2006 | O'Lenick, Jr. |
| 8,017,818 B2 * | 9/2011 | Cortright et al. ............ 585/240 |
| 2008/0300435 A1 | 12/2008 | Cortright |
| 2008/0302001 A1 | 12/2008 | Koivusalmi et al. |
| 2010/0094062 A1 | 4/2010 | Rabello et al. |

OTHER PUBLICATIONS

Klepacova, K., et al., "Etherification of Glycerol and Ethylene Glycol by Isobutylene." Applied Catalysis A: General 328: 1-13 (2007).
Klepacova, K., et al., "tert-Butylation of Glycerol Catalyzed by Ion-Exchange Resins." Applied Catalysis A: General 294: 141-147 (2005).
Karinen, R. et al., "New Biocomponents from Glycerol" Applied Catalysis A: General 306: 128-133 (2006).
Frusteri, F., et al., "Catalytic Etherification of Glycerol by tert-Butyl Alcohol to Produce Oxygenated Additives for Diesel Fuel." Applied Catalysis A: General 367: 77-83 (2009).
Tijm, P. et al., "Effect of Oxygenated Cetane Improver on Diesel Engine Combustion & Emissions" http://www.energy.psu.edu/tr/cetane.html, Mar. 2, 2012.
Murphy, M. et al., "Compendium of Experimental Cetane Number Data" NREL/SR-540-36805 (2004). http://www.nrel.gov/vehiclesandfuels/pdfs/sr368051.pdf.

* cited by examiner

*Primary Examiner* — Tam M Nguyen
(74) *Attorney, Agent, or Firm* — Phillips 66 Company

(57) ABSTRACT

The present disclosure relates to methods for converting biomass-derived streams of hydrocarbon diols into products suitable for use as a biomass-derived fuel additive. These methods involve the condensation of diols comprising five or six carbon atoms to form condensation products containing at least ten carbon atoms. The remaining hydroxyl functional groups of the condensation products are optionally modified to decrease overall polarity of the products, and improve miscibility with liquid hydrocarbon mixtures.

10 Claims, 2 Drawing Sheets

US 8,497,403 B2

CONDENSATION OF DIOLS FOR BIOFUEL PRODUCTION

CROSS-REFERENCE TO RELATED APPLICATIONS

This application is a non-provisional application which claims benefit under 35 USC §119(e) to U.S. Provisional Application Ser. No. 61/424,775 filed Dec. 20, 2010, entitled "CONDENSATION OF DIOLS FOR BIOFUEL PRODUCTION," which is incorporated herein in its entirety and U.S. Provisional Application Ser. No. 61/438,299 filed Feb. 1, 2011 entitled "CONDENSATION OF DIOLS FOR BIOFUEL PRODUCTION," which is incorporated herein in its entirety.

STATEMENT REGARDING FEDERALLY SPONSORED RESEARCH OR DEVELOPMENT

None.

FIELD OF THE INVENTION

The present disclosure relates to the field of biomass-derived transportation fuels. More specifically, the present disclosure relates to processes for converting diols originating from biomass into products suitable for use as fuel additives Acidic condensation reactions are utilized to convert biomass-derived diols into polyether products suitable for use as oxygenated hydrocarbon fuel additives.

BACKGROUND

Over the last decade, there has been an increasing interest in discovering alternative sources of fuels and chemicals from resources other than petroleum. Development of non-petroleum-based fuels may provide economic and environmental benefits, while also increasing national security by decreasing reliance on non-domestic energy sources. Biomass, such as plants and animal fats, represent a major alternative source of hydrocarbons that can be converted into fuels. Liquid fuels derived from biomass are rapidly entering the market, driven by both need for increased national energy independence and rapid fluctuations in the cost of petroleum products. In 2007, the Energy Independence and Security Act was passed in the United States, which requires increasing quantities of bio-derived fuels to be produced over time. Similarly, the European Union directive 2003/30/EC promotes the use of biofuels or other renewable fuels. The directive has set a minimum percentage of biofuels to replace diesel or gasoline for transport purposes, such that by 2011 a 5.75% minimum proportion of Biofuels will be required in all gasoline and diesel fuels sold. Thus, it is essential to develop more efficient processes to convert bio-derived compounds into fuels that can fulfill these government mandates, as well as future global energy needs.

The carbohydrates found in plants and animals can be used to produce fuel range hydrocarbons. However, many carbohydrates (e.g., starch) are undesirable as feed stocks for creating biomass-derived fuels due to the costs associated with converting them to a usable form. The chemical structure of some carbohydrates makes them difficult to convert, and conversion processes may produce low yields of desirable products. Carbohydrates that are difficult to convert include compounds with low effective hydrogen to carbon ratios, including carbohydrates such as starches and sugars, as well as other oxygenates with low effective hydrogen ratios such as carboxylic acids and anhydrides, light glycols, glycerin and other polyols and short chain aldehydes. Therefore, development of an efficient and inexpensive process for converting one or more of these difficult-to-convert biomass feedstocks into a form suitable for use as an oxygenated fuel additive could be a significant contribution to the art and to the economy.

The first step in processing biomass is to cleave larger structures down to their component subunits. Some processes, such as acid hydrolysis, can release the smaller pentose and hexose subunits from larger structures such as cellulose and starch. Because these sugars are inherently five to six carbons in length, a complete deoxygenation process yields saturated hydrocarbons having boiling points in the gasoline "boiling-range" (i.e., about 27° C. to 190° C.). Unfortunately, limited options are available for the upgrading/conversion of saturated five and six carbon hydrocarbons, and no options currently exist for converting these materials into liquid hydrocarbon fuels that boil in the diesel range in conventional refining units. Alternatively, partial deoxygenation of these sugars leaves some oxygen in the starting material, providing a variety of opportunities for upgrading due to the numerous chemical reactions that oxygenates may undergo.

Several partially-deoxygenated intermediates are available in these biomass feeds that may be converted to products useful as oxygenated fuel additives. One class of intermediates includes five and six carbon diols derived from pentose and hexose sugars. These diols are not suitable for direct blending into fuels as they have a low cetane number, as well as low miscibility in hydrocarbon fuels.

Condensation reactions are one way to assemble oxygenates into larger compounds. Condensation allows the conversion of small bio-derived feedstocks into a larger size that is better-suited for use as a fuel additive. Several groups have reported the conversion of certain biomass-derived feedstocks via condensation reactions. A paper by Karinen, et. al. pertains to the etherification of glycerol and isobutene, while papers by Frustieri, et. al. and Keplacova, et. al, both report methods for catalytic etherification of glycerol by tert-butyl alcohol. US2010/0094062 describes a process for the etherification of glycerol with an alkene or alkyne, followed by nitration of a remaining hydroxyl group. A portion of the process claimed in US2008/0300435 pertains to the dimerization/condensation of monofunctional alcohols such as pentanol or isopropyl alcohol, while US2008/0302001 pertains to methods for producing biofuels that include several types of condensation reactions, including the Guerbet alcohol condensation, but not an acidic condensation of two hydroxyls to form an ether. To date, no methods have demonstrated an efficient process for the acid condensation of a feedstock comprising diols containing five and six carbons to produce an oxygenated fuel additive.

BRIEF SUMMARY

The present disclosure provides processes through which diols derived from biomass containing five and six carbons can participate in multiple condensation reactions to yield an ether (or polyether) product containing at least ten carbons. This is followed by either excess oxygen removal or hydroxyl capping to increase miscibility of the product with liquid hydrocarbons. The mostly linear products contain oxygen periodically substituted for methylene units ($-CH_2-$) along their backbone and are thus often suitable for use as oxygenated fuel additives. Indeed, certain ethers have been shown to improve the ignition properties of transportation fuels; properties that may include increasing cetane number and reducing particulate emissions, when compared to currently-produced premium fuels. For example, a compendium by Murphy, et al. shows that a variety of ethers have been calculated to have a high cetane number.

The present disclosure pertains to utilizing acid-catalyzed condensation reactions to convert biomass-derived diols into polyethers containing between ten and twenty-four carbons, followed by steps to increase miscibility of the polyether with liquid hydrocarbon fuels. The final products of the process are useful as fuel additives for diesel or kerosene-type fuels. During the conventional processing of hydrocarbons to produce fuels, removing oxygen involves reacting oxygen containing compounds with hydrogen to produce water. In contrast, the chemistry behind the inventive process involves acid-catalyzed condensation reactions that do not require hydrogen for oxygen removal. Typical refining processes remove oxygen from feeds by consuming hydrogen. However, hydrogen is expensive and its production generates carbon dioxide. Thus, reducing the need for hydrogen in the process decreases operational cost associated with production of hydrogen, as well as the carbon footprint in the production of biofuels. Some oxygen from the starting material is left in the final product, resulting in the product maintaining much of its original volume. Finally, these condensation reactions may be conducted at much lower temperatures than conventional oxygen removal processes, resulting in further savings.

Certain embodiments disclosed herein provide a process for converting a biomass-derived diol feedstock possessing five or six carbons (such as, 1,4-pentanediol or 1,5-pentanediol) into products suitable for use as fuel additives that comprises the steps of: (a) providing a biomass-derived feedstream comprising hydrocarbon diols that contain five or six carbon atoms, (b) contacting the feedstream with a first catalyst in a reactor, where the contacting results in an acidic condensation reaction that converts a least a portion of the feedstream to condensation products that contain at least 10 carbon atoms and at least one ether functional group, (c) converting at least a portion of the remaining hydroxyl functional groups on the condensation products to ether functional groups by combining the condensation products with a second catalyst to produce a liquid hydrocarbon mixture suitable for use as an additive to liquid hydrocarbon fuels, where the conversion takes place in the presence of an olefin, a monofunctional alcohol or mixtures of these, and where as a result of this conversion, the liquid hydrocarbon mixture has increased miscibility in liquid hydrocarbon fuels as a result.

Certain embodiments further comprise the step of combining the liquid hydrocarbon mixture of step (c) with a liquid hydrocarbon fuel to produce an improved liquid hydrocarbon fuel possessing improved combustion properties that may include increasing the cetane number of the fuel, decreasing the emission of environmental pollutants during combustion, or both.

In certain alternative embodiments, step (c) involves reducing at least a portion of the remaining hydroxyl groups on the condensation products by combining the condensation products with a second catalyst in the presence of hydrogen to produce water and a liquid hydrocarbon mixture that is suitable for use as a fuel additive that has increased miscibility in liquid hydrocarbon fuels as a result of this reduction step. In certain embodiments, the functions of the first and second catalyst are performed by the same catalyst.

BRIEF DESCRIPTION OF THE DRAWINGS

Advantages of the present invention will become apparent to those skilled in the art with the benefit of the following detailed description and upon reference to the accompanying drawing.

DETAILED DESCRIPTION

Figure 1:
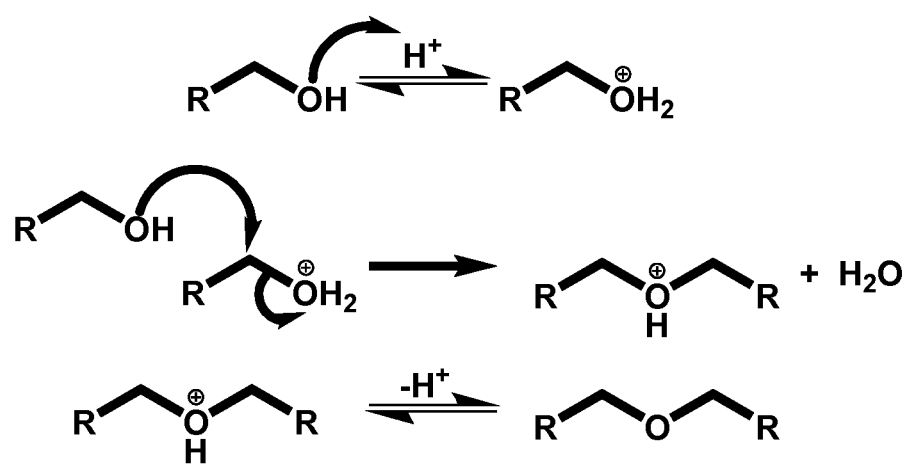
FIG. 1 is a simplified schematic depicting an acidic condensation reaction for converting two primary hydroxyl groups into an ether bond, in accordance with certain embodiments of the present disclosure.

Process conditions for conducting condensation reactions are relatively mild when compared to other industrial processes, such as conventional naphtha hydrodesulfurization, which normally requires temperatures in the range of 285° C. to 370° C. Low temperatures are advantageous since at higher temperature elimination becomes a competing reaction mechanism. Elimination, like condensation, involves the removal of a small molecule from a parent, but there is no coupling associated with the reaction. Elimination results in the production of an unsaturated product (e.g., ethanol to ethylene.) While these limits exist, yields for this process are typically sufficient to operate at the commercial level for chemical production. The acidic condensation of the current disclosure could also be referred to as etherification, and is illustrated in FIG. 1. The acid catalyst donates a proton to a hydroxyl group of a first glycol molecule, allowing a hydroxyl group from a second glycol molecule to form an ether bond with the electrophilic carbon adjacent to the proton-accepting hydroxyl. A water molecule (and proton) are removed, and an ether bond is formed between the two glycols. Acid-catalyzed condensation of primary alcohols in the homogeneously catalyzed case occurs via an $S_N2$ mechanism. In this type of mechanism, the transition state involves the attacking nucleophile driving off the leaving group in a concerted mechanism. This acid-catalyzed condensation (or etherification) reaction is distinct from the base-catalyzed condensation reaction developed by Guerbet, which instead produces branched, saturated alcohols and not ethers. Examples of the Guerbet condensation reaction being utilized to form saturated branched hydrocarbons are shown in U.S. Pat. No. 7,049,476 and US2008/0302001.

Using solid acids as catalyst, it is possible to convert diols containing five or six carbons into ether (or polyether) products. Certain derivatives of these products fall into a category of materials termed oxygenated fuel additives. Oxygenated fuel additives are larger, predominantly linear compounds with oxygen substituted for carbon periodically along the backbone. Some have shown promise by increasing overall cetane number of the fuel, reducing particulate emissions resulting from combustion, or both. For example, a National Renewable Energy Laboratory report by Murphy, et al. shows that number of polyglycols have been calculated to possess a high cetane number. In addition, preliminary findings by Tijm, et al. have shown that several polyether compounds, when added to premium diesel fuel at 10-11% (by wt.), reduce particulate emissions during combustion by up to 28%.

The condensation reactions associated with the processes described herein are generally conducted at a temperature ranging from about 100° C. to about 300° C. More preferably, these reactions are conducted at a temperature ranging from about 120° to about 260° C. The condensation reactions are generally conducted at a pressure ranging from about 200 kPa to about 8000 kPa. More preferably, reactions are conducted at a pressure ranging from about 500 kPa to about 5000 kPa. Additionally, condensation reactions of the present disclosure are generally conducted with a feedstream flow rate ranging from about 0.1 $h^{-1}$ liquid weight hourly space velocity (LWHSV) to about 20 $h^{-1}$ LWHSV. More preferably, reactions are conducted with a feedstream flow rate ranging from about 0.5 $h^{-1}$ LWHSV to about 15 $h^{-1}$ LWHSV.

The strong acid digestion of biomass not only can cleave carbohydrates into smaller sugars, but also removes some of the oxygen from the product. This process leaves unsaturated, ringed products that can be hydrotreated with noble metal catalysts to produce diols that may include, for example, 1,3-pentanediol, 1,4-pentanediol, 1,5-pentanediol, 1,3-hexanediol, 1,4-hexanediol, 1,5-hexanediol and 1,6-hexanediol. The feedstock for the acidic condensations of the current disclosure may comprise a mixture containing one or more of the above-listed biomass-derived diols. Preferably, the diol feedstock comprises 1,4-pentanediol, 1,5-pentanediol, or mixtures thereof that are derived from biomass.

We utilized 1,5-pentanediol as a test compound to demonstrate certain embodiments of the current invention. 1,5-pentanediol mimics the condensation propensity of 1,4-pentanediol, as both contain primary alcohol groups. These primary alcohol groups are the most active for condensation while avoiding other unfavorable acid-catalyzed reactions. Cyclization may occur when two hydroxyl groups are present in the starting compound, and these hydroxyls are separated by at least three carbons, such that a condensation reaction between these functional groups is not sterically-hindered. With 1,5-pentanediol, this cyclization produces tetrahydropyran (THP), a gasoline-range product that possesses poor fuel properties. Although 1,4-pentanediol cannot form a six-member ring such as THP, it can instead form methyltetrahydrofuran (MTHF), a five-member ring. Like THP, MTHF is a gasoline-range compound with poor fuel properties. If the condensation catalyst utilized is not largely selective for the production of linear condensation products, the yields of THP and MTHF can be significant, thereby limiting the usefulness of the reaction. Therefore, preventing cyclization is key for the successful large-scale viability of any process that proposes to condense feeds that are capable of forming five- or six-member rings into products useful as fuel additives.

Figure 2:
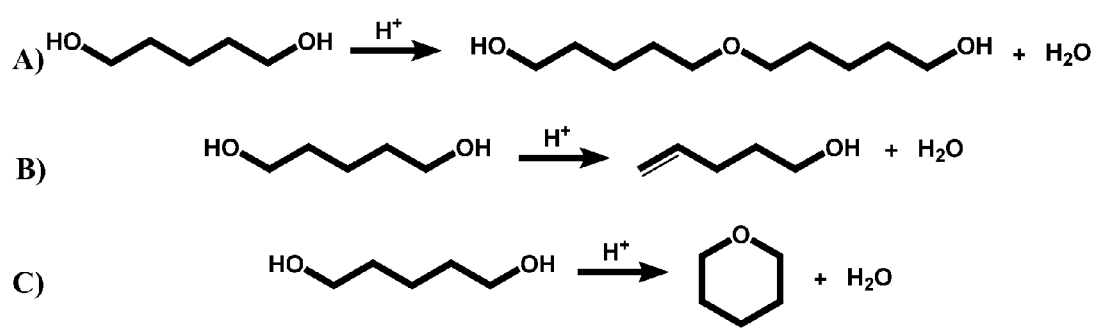
FIG. 2 is a simplified schematic depicting various chemical reactions of 1,5-pentanediol that can occur in the presence of an acidic catalyst, in accordance with certain embodiments of the present disclosure The invention is susceptible to various modifications and alternative forms, specific embodiments thereof are shown by way of example in the drawings. The drawings may not be to scale. It should be understood that the drawings and their accompanying detailed descriptions are not intended to limit the scope of the invention to the particular form disclosed, but rather, the intention is to cover all modifications, equivalents and alternatives falling within the spirit and scope of the present invention as defined by the appended claims.

Potential reaction pathways for a 1,5-pentanediol feedstock in the presence of an acid catalyst are shown in FIG. 2. A condensation reaction that forms an ether product containing ten carbon atoms is shown in FIG. 2A. An additional condensation reaction between this product and 1,5-pentanediol produces a polyether containing 15 carbons (not depicted). FIG. 2B depicts a pathway for the dehydration of 1,5-pentanediol to form a mono-alcohol that can still participate in a condensation reaction. FIG. 2C depicts the intramolecular cyclization of 1,5-pentanediol to form the undesirable product THP. While each depicted reaction pathway successfully removes oxygen without consuming hydrogen, the THP produced by the pathway shown in FIG. 2C is not useful as a fuel additive.

Condensation catalysts useful with the current invention include any catalyst capable of condensing diols comprising five or six carbon atoms to produce an ether (or polyether) containing at least 10 carbon atoms. Preferably, the catalyst is an acidic catalyst capable of conducting acidic condensation reactions as depicted in FIG. 1 and FIG. 2A. Preferably, the condensation catalyst utilized has selectivity for the formation of linear products. More preferably, the catalyst is a microporous molecular sieve selected from crystalline silicoaluminophosphates and aluminosilicates (such as, for example, H-Y, H-USY, H-mordenite, or H-ZSM-5) possessing a three-dimensional pore structure that selectively favors the production of linear condensation products within the pores of the catalyst, while minimizing production of undesirable cyclic secondary products derived by the intra-molecular cyclization of diols containing five or six carbons (see FIG. 2C). The size of the catalyst pores may be adjusted through ion-exchange, catalytic cracking of silane, or any other method commonly known in the art. As a result, intra-molecular cyclization of diols to form bulky, cyclic side-products is less likely to occur within the confines of the molecular sieve channel system.

In certain embodiments, the catalyst is a microporous molecular sieve catalyst (as described above) that is surface-passivated to inhibit catalytic activity outside of the channel system, thereby further selecting against the intramolecular cyclization of the feedstock to form side products. Methods for surface passivation of molecular sieves are familiar to those with knowledge in the art, and one example of a typical passivation procedure is provided in Example II of the current disclosure. Creating selectivity towards the favored products is important for the economic viability of the process at industrial scale, since the cyclic side-products (such as THP or MTHF) are unsuitable for blending into fuels, and are stable products that are difficult to convert back to a form with commercial value.

Optionally, following condensation of the diol feedstock to form an ether (or polyether), remaining hydroxyl groups are modified by an additional step that reacts them with an olefin to form ether bonds. This step is primarily intended to increase misibility of the product with hydrocarbon fuels, but may also serve to further increase the cetane number of the product. The step may be accomplished by any catalyst that promotes an etherification reaction between the remaining terminal hydroxyl groups and an olefin. In certain embodiments, the catalyst may be an acidic macroreticular ion-exchange reaction, such as Amberlyst™ 15 or 35 (Rohm and Hass) type resins. Such capping techniques are understood by individuals having knowledge in the art, and examples of such techniques are provided in the previously mentioned papers by Karinen, et. al., Frustieri, et. al. and Keplacova, et al.

In certain alternative embodiments, the remaining hydroxyl groups that are present on the product ether (or polyether) following condensation of the diol feed are instead "capped" by an additional acidic condensation reaction in the presence of a small monofunctional alcohol (such as, for example, methanol, ethanol or propanol). This step may be performed with any catalyst capable of catalyzing an etherification reaction between the remaining terminal hydroxyl groups of the ether (or polyether) and the monofunctional alcohol. The monofunctional alcohol has only one functional group capable of participating in a further round of etherification, thus effectively preventing further growth of the polymer. The end product would preferably have increased miscibility in liquid hydrocarbon fuels, and thus, be more suitable for use as a fuel additive.

In still other embodiments, the remaining hydroxyl groups that are present on the product ether (or polyether) following condensation of the diol feed are instead "capped" by mild hydrodeoxygenation (HDO) of the remaining hydroxyl functional groups. It is important that the HDO step be mild so as to not completely remove all oxygen from the ether (or polyether), as a certain amount of oxygen in the final product is desirable. This HDO step may be catalyzed by any of a number of commercially available catalysts, including commercial hydrotreating catalysts comprising Co and Mo, or Ni and Mo. Procedures for conducting such HDO reactions are commonly known in the art. The end product would preferably have increased miscibility in liquid hydrocarbon fuels, and thus, be more suitable for use as a fuel additive.

EXAMPLES

The following examples are each intended to be illustrative of a specific embodiment of the present invention in order to teach one of ordinary skill in the art how to make and use the invention. It is not intended to limit the scope of the invention in any way.

Example I

ZSM-5 (Si/Al=15) extrudates were obtained from Zeolyst International. Extrudates were crushed and sieved to −20/+40 mesh. $NH_4$-ZSM-5 was converted into the acidic form (H-ZSM-5) by calcining in a muffle furnace under flowing air. Excess air was flowed over the catalyst while the samples were heated using a gradual heat/soak temperature profile. Samples were heated to 150° C. at 2° C./min, maintained at 150° C. for 2 hours, then heated to 450° C. at 4° C./min. Samples were maintained at the final temperature overnight (>12 hours.)

Catalyst was dried in-situ at the specified operating temperature for a minimum of 30 minutes in flowing $N_2$ prior to each run. Except as noted, runs were performed at a constant liquid feed rate of 10 mL/hr, using 98% 1,5-pentanediol obtained from Sigma-Aldrich. Runs had no gas flow, though the reactor was brought up to pressure with $N_2$. Liquid samples were taken at one hour intervals for five hours following the first collection of products. Liquid samples were collected in a Swagelok 1000 mL sample cylinder. Samples were analyzed on an Agilent 7890A gas chromatograph (GC) equipped with a 7863B Autoinjector Module, a HP-5 capillary column, and FID detection. Conversions, yields, and selectivities were determined by averaging the values from the last 3 hours of each run. Ambient temperature, non-condensable products were analyzed on-stream using a HP-5 capillary column with a flame ionization detector (FID).

Example II

Hypothetical Example: Passivation of a Zeolite Catalyst with Either Poly(phenylmethyl)siloxane or Tetraethylorthosilicate: Zeolite catalysts useful in certain embodiments of the invention may be chemically-modified to passivate (i.e., block active sites on) the surface of the catalyst, thereby increasing selectivity for the production of LMW poly-glycols. One examples of how this can be achieved is outlined in U.S. Pat. No. 6,228,789, which pertains to a method for silylation of zeolite catalysts and is incorporated herein by reference.

A zeolite H-ZSM-5 is contacted to incipient wetness with a 50 wt % solution of Poly(phenylmethyl)siloxane (PPMS) in cyclohexane, and the catalyst is not pre-calcined prior to contacting. After impregnation of the catalyst, it is dried and calcined at 538° C. for 6 hrs. Alternatively, the H-ZSM-5 catalyst is impregnated with a 50 wt. % solution of Tetraethylorthosilicate (TEOS) under conditions identical to those used for impregnation with PPMS.

Example III

Catalytic Conversion Test Conditions: Unless otherwise noted, Catalytic data were acquired using a ¾" down-flow reactor. A bed of glass beads prior to the catalyst bed preheated the feed to reaction temperature. Prescribed amounts of catalyst were diluted in an inert material (alundum) to a constant volume of 20 mL to ensure homogeneous temperature distribution. Loaded reactors were heated using a three-zone Thermcraft furnace with independent temperature control for each zone. Liquid feed was delivered to the system by an ISCO 1000D syringe pump. The system pressure was controlled by a Tescom backpressure regulator. Samples were taken at one hour intervals, and conversion and selectivity percentages (unless otherwise noted) were calculated by averaging data obtained from three different samples taken at different time points.

Example IV

Table I presents data for the conversion of 1,5-pentanediol over H-ZSM-5 catalyst. Data included are the overall percent conversions (Column 2), percent selectivity toward formation of the desired linear condensation products (Column 3) and selectivity to the undesired cyclization product, tetrahydropyran (Column 4). At mild temperatures (175° C.), condensation occurs readily for this system. The highest conversion observed was 58.8%. Gas chromatography (GC) identified dipentanediol, tripentanediol, and tetrapentanediol as the main desired products, with the amount of each oligomer produced varying inversely with increasing size of the product. Yields to the tetramer were low, which is beneficial, since this large product would likely have cold flow problems. It is more desirable to produce dimers and trimers, as these products are in the distillate boiling range and should not suffer low temperature flow issues. In this case, it is a balancing act between obtaining a desirable extent of condensation to afford diesel-range products, but not taking the products so far as to go into the gas oil boiling range. No gaseous products were observed.

The condensation of 1,5-pentanediol also produced the undesirable tetrahydropyran, formed from the intramolecular cyclization of the feedstock. (see FIG. 2C). On average, 56.5% of 1,5-pentanediol was converted, but only 22.2% of the feedstock was converted to linear products. Intra-molecular cyclization of the diol feedstock appeared to be the most likely pathway for THP formation

TABLE 1

Conversion of 1,5-pentanediol over H-ZSM-5 at various reaction conditions.

| Run | % Conversion | % Selectivity to Linear Condensation Products | % Selectivity to THP | Temp. (° C.) | Pressure (KPa) | LWHSV (hr$^{-1}$) |
|---|---|---|---|---|---|---|
| 1 | 0.6 | 17 | 54 | 127 | 689 | 15.0 |
| 2 | 15.1 | 33 | 60 | 176 | 2758 | 15.0 |
| 3 | 58.7 | 46 | 47 | 176 | 689 | 1.5 |
| 4 | 1.1 | 11 | 63 | 154 | 1724 | 8.3 |
| 5 | 7.8 | 40 | 54 | 127 | 2758 | 1.5 |
| 6 | 2.3 | 13 | 65 | 176 | 2758 | 15.0 |
| 7 | 7.2 | 38 | 56 | 128 | 2758 | 1.5 |
| 8 | 54.1 | 32 | 60 | 178 | 689 | 1.5 |
| 9 | 4.7 | 44 | 41 | 151 | 1724 | 8.3 |
| 10 | 0.8 | 26 | 53 | 128 | 689 | 15.0 |

DEFINITIONS

As used herein, the term "liquid weight hourly space velocity" or "LWHSV" refers to the liquid weight hourly space velocity.

As used herein, the term "cetane" or "cetane number" refers to the cetane number of a fuel as measured by the ASTM (American Society for Testing and Materials) D613 or D6890 standard.

As used herein, the term "fuel" refers to any liquid hydrocarbon mixture used to power an engine, including gasoline, diesel and jet fuels.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed and certain features of the invention may be utilized independently, all as would be apparent to one skilled in the art after having the benefit of this description of the invention. Changes may be made in the elements described herein without departing from the spirit and scope of the invention as described in the following claims.

REFERENCES

All of the references cited herein are expressly incorporated by reference. Incorporated references are listed again here for convenience:
1. US2010/0094062 (Rabello; Ferreiral; Menenzes); "Cetane Number Increasing Process and Additive for Diesel Fuel."
2. US2008/0300435 (Cortright; Blommel); "Synthesis of Liquid Fuels and Chemicals From Oxygenated Hydrocarbons."
3. US2008/0302001 (Koivusalmi; Piiola; Aalto) "Process for Producing Branched Hydrocarbons."
4. U.S. Pat. No. 7,049,476 (O'Lenick, Jr.) "Guerbet Polymers" (2006).
5. U.S. Pat. No. 6,228,789 (Wu; Drake) "Silylated Water Vapor Treated Zinc or Gallium Promoted Zeolite and Use Thereof for the Conversion of Non-aromatic Hydrocarbons to Olefins and Aromatic Hydrocarbons" (2001).
6. Klepacova, K., et al., "Etherification of Glycerol and Ethylene Glycol by Isobutylene." Applied Catalysis A: General 328: 1-13 (2007).
7. Klepacova, K., et al., "tert-Butylation of Glycerol Catalyzed by Ion-Exchange Resins." Applied Catalysis A: General 294: 141-147 (2005).
8. Karinen, R. et al., "New Biocomponents from Glycerol" Applied Catalysis A: General 306: 128-133 (2006).
9. Frusteri, F., et al., "Catalytic Etherification Of Glycerol By tert-Butyl Alcohol To Produce Oxygenated Additives For Diesel Fuel." Applied Catalysis A: General 367: 77-83 (2009).
10. Tijm, P. et al., "Effect of Oxygenated Cetane Improver on Diesel Engine Combustion & Emissions" http://www.energy.psu.edu/tr/cetane.html
11. Murphy, M. et al., "Compendium of Experimental Cetane Number Data" NREL/SR-540-36805 (2004). http://www.nrel.gov/vehiclesandfuels/pdfs/sr368051.pdf

I claim:

1. A process comprising the steps of:
   (a) providing a biomass-derived feedstream comprising hydrocarbon diols that contain five or six carbon atoms;
   (b) contacting the feedstream of step (a) with a first catalyst in a reactor, wherein the contacting results in an acidic condensation reaction that converts a least a portion of the feedstream to condensation products, wherein said condensation products comprise at least 10 carbon atoms and at least one ether functional group;
   (c) converting at least a portion of the remaining hydroxyl functional groups on the condensation products from step (b) to ether functional groups by combining the condensation products with a second catalyst to produce a liquid hydrocarbon mixture suitable for use as an additive to liquid hydrocarbon fuels,
      wherein the converting takes place in the presence of an olefin, monofunctional alcohol or mixtures thereof,
      wherein the liquid hydrocarbon mixture has increased miscibility in liquid hydrocarbon fuels as a result of step c).

2. The process of claim 1, wherein the feedstream of step (a) comprises a member selected from the group consisting of 1,3-pentanediol, 1,4-pentandiol, 1,5-pentanediol, 1,3-hexanediol, 1,4-hexandiol, 1,5-hexanediol and 1,6-hexanediol and mixtures thereof.

3. The process of claim 1, further comprising combining the liquid hydrocarbon mixture of step (c) with a liquid hydrocarbon fuel to produce a improved liquid hydrocarbon fuel,
   wherein the improved liquid hydrocarbon fuel has improved combustion properties relative to the original liquid hydrocarbon transportation fuel,
   wherein said combustion properties comprise a member selected from the group consisting of increased cetane number, decreased emissions of environmental pollutants during combustion and combinations thereof.

4. The process of claim 1, wherein the contacting of step (b) is conducted at a temperature in the range of about 100° C. to about 300° C., and at a pressure in the range of about 200 kPa to about 8000 kPa.

5. The process of claim 1, wherein the contacting of step (b) is conducted at a temperature in the range of about 120° C. to about 260° C., and at a pressure in the range of about 500 kPa to about 5000 kPa.

6. The process of claim 1, wherein the contacting of step (b) is conducted at a feedstream flow rate in the range of about 0.1 h$^{-1}$ LWHSV to about 20 h$^{-1}$ LWHSV.

7. The process of claim 1, wherein the contacting of step (b) is conducted at a feedstream flow rate in the range of about 0.5 $h^{-1}$ LWHSV to about 15 $h^{-1}$ LWHSV.

8. The process of claim 1,
wherein the functions of the first catalyst and the second catalyst are performed by the same catalyst.

9. The process of claim 1,
wherein the first catalyst is a microporous molecular sieve selected from the group consisting of crystalline silicoaluminophosphates and aluminosilicates,
wherein said molecular sieve has been chemically treated to prevent catalytic activity outside the internal channels of the catalyst,
wherein the pore diameter of said molecular sieve restricts the catalytic formation of circular products inside the pores of the molecular sieve.

10. The process of claim 1, wherein the second catalyst comprises an acidic macroreticular ion-exchange resin.

* * * * *